(12) United States Patent
Dwight et al.

(10) Patent No.: US 10,093,806 B2
(45) Date of Patent: Oct. 9, 2018

(54) METHODS FOR SYNTHESIZING RHODAMINE DYES

(71) Applicant: PROMEGA CORPORATION, Madison, WI (US)

(72) Inventors: Stephen J. Dwight, Arroyo Grande, CA (US); Sergiy Levin, San Luis Obispo, CA (US)

(73) Assignee: PROMEGA CORPORATION, Madison, WI (US)

( * ) Notice: Subject to any disclaimer, the term of this patent is extended or adjusted under 35 U.S.C. 154(b) by 19 days.

(21) Appl. No.: 15/282,590

(22) Filed: Sep. 30, 2016

(65) Prior Publication Data

US 2017/0096560 A1    Apr. 6, 2017

Related U.S. Application Data

(60) Provisional application No. 62/236,488, filed on Oct. 2, 2015.

(51) Int. Cl.
*C09B 11/24* (2006.01)

(52) U.S. Cl.
CPC .................................. *C09B 11/24* (2013.01)

(58) Field of Classification Search
CPC ....................................................... C09B 11/24
See application file for complete search history.

(56) References Cited

U.S. PATENT DOCUMENTS 9,056,885 B2    6/2015  Kirkland et al.
2012/0135459 A1    5/2012  Hell et al.

FOREIGN PATENT DOCUMENTS

WO    2009/046165    4/2009

OTHER PUBLICATIONS

International Search Report and Written Opinion for Application No. PCT/US2016/054898 dated Nov. 25, 2016 (10 pages).
Beija et al., "Synthesis and applications of Rhodamine derivatives as fluorescent probes," Chem. Soc. Rev., 2009, 38, 2410-2433.
Kvach et al., "Practical Synthesis of Isomerically Pure 5- and 6-Carboxytetramethylrhodamines, Useful Dyes for DNA Probes," Bioconjugate Chem. 2009, 20, 1673-1682.
Yu et al., "From Spirolactam Mixtures to Regioisomerically Pure 5- and 6-Rhodamines: A Chemodosimeter-Inspired Strategy," Org. Lett., 2012, 14 (8), pp. 2014-2017.

*Primary Examiner* — Noble E Jarrell
(74) *Attorney, Agent, or Firm* — Michael Best & Friedrich LLP

(57) ABSTRACT

Described herein are methods for the regioselective synthesis of substituted rhodamine dyes.

20 Claims, No Drawings

METHODS FOR SYNTHESIZING RHODAMINE DYES

CROSS-REFERENCE TO RELATED APPLICATIONS

This application claims priority to U.S. Provisional Patent Application No. 62/236,488, filed on Oct. 2, 2015, the entire contents of which are incorporated by reference herein.

TECHNICAL FIELD

The present disclosure relates generally to methods for the regioselective synthesis of rhodamine dyes.

BACKGROUND

Rhodamine dyes are widely used in biotechnology applications including fluorescence microscopy, flow cytometry, and enzyme-linked immunosorbent assays (ELISA). However, current methods for the synthesis of certain rhodamine dyes, such as 6-carboxyrhodamines, include drawbacks such as the requirement for harsh reaction conditions, production of multiple isomers, the need for extensive purification procedures, and low yields.

SUMMARY

In one aspect, disclosed is a method of synthesizing a rhodamine dye, the method comprising:
reacting a compound of formula (I):

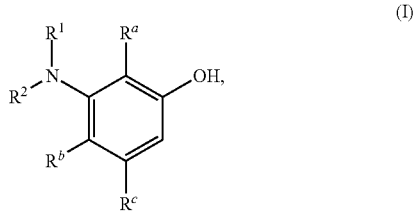

(I)

wherein $R^1$ and $R^2$ are each independently hydrogen, alkyl, or $R^{1a}$—CO—, wherein $R^{1a}$ is hydrogen, $C_1$-$C_4$ alkyl (e.g., tBu), $C_1$-$C_4$ haloalkyl (e.g., $CF_3$, $CHF_2$), or $C_1$-$C_4$ alkoxy; or $R^1$ and $R^2$, together with the atoms to which they are attached, form a 3-8 membered ring; $R^c$ is selected from the group consisting of hydrogen, alkyl, alkoxy, haloalkyl and halogen; and $R^a$ and $R^b$ are each independently selected from the group consisting of hydrogen, alkyl, alkoxy, haloalkyl and halogen; or $R^1$ and $R^a$, together with the atoms to which they are attached, form a 5-8 membered ring, and $R^2$ and $R^b$, together with the atoms to which they are attached, form a 5-8 membered ring;
with a compound of formula (II),

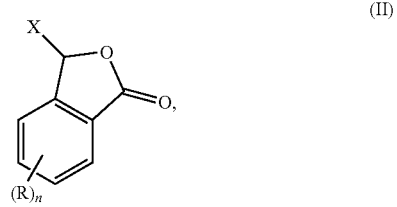

(II)

wherein R is selected from the group consisting of halogen, alkyl, haloalkyl, cyano, carboxy, alkoxy, haloalkoxy, alkoxycarbonyl, (carboxy)heteroalkyl, alkylcarbonyl, alkoxyalkyl, cycloalkyl, aryl, arylalkyl, heteroaryl, heteroarylalkyl, sulfonate, sulfonamide and amide; n is 0, 1, 2, 3 or 4; X is halogen or $OR^3$; and $R^3$ is selected from the group consisting of hydrogen, alkyl, aryl, alkylcarbonyl, alkoxycarbonyl, haloalkyl, haloalkylcarbonyl, haloalkoxycarbonyl, alkylsulfonyl, arylsulfonyl and haloalkylsulfonyl; to form the rhodamine dye.

DETAILED DESCRIPTION

Disclosed herein are regioselective methods for synthesizing rhodamine dyes. Whereas classical syntheses use cyclic anhydrides (e.g. 1,2,4-benzenetricarboxylic anhydride, also known as trimellitic anhydride) as a starting material, these reactions result in production of a mixture of isomers. The syntheses disclosed herein involve the use of an optionally substituted phthalaldehydic acid or phthalaldehydic acid derivative. This approach can provide rhodamines in high yield under mild conditions and in isomerically pure form. The methods disclosed herein may therefore allow for faster and less expensive production of certain substituted rhodamine dyes.

1. Definition of Terms

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terminology used herein is for the purpose of describing particular embodiments only and is not intended to be limiting. As used in the specification and the appended claims, the singular forms "a," "and" and "the" include plural references unless the context clearly dictates otherwise.

For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used herein, the term "about" is used synonymously with the term "approximately." Illustratively, the term "about," as used in connection with a particular value, indicates that the value may be slightly outside the particular value. Variation may be due to conditions such as experimental error, manufacturing tolerances, variations in equilibrium conditions, and the like. In some embodiments, the term "about" includes the cited value plus or minus 10%. Such values are thus encompassed by the scope of the claims reciting the terms "about" and "approximately."

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkyl" as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_3$-$C_7$ branched alkyl" means a branched chain hydrocarbon containing from 3 to 7 carbon atoms. The term "$C_1$-$C_4$-alkyl" means a straight or branched chain hydrocarbon containing from 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkoxyalkyl" as used herein, refers to an alkoxy group, as defined herein, appended to the parent molecular moiety through an alkyl group, as defined herein.

The term "alkoxycarbonyl" as used herein, refers to an alkoxy group, as defined herein, appended to the parent molecular moiety through a carbonyl.

The term "alkylcarbonyl" as used herein, refers to an alkyl group, as defined herein, appended to the parent molecular moiety through a carbonyl.

The term "alkylsulfonyl" as used herein, refers to an alkyl group, as defined herein, appended to the parent molecular moiety through a sulfonyl.

The term "alkoxyfluoroalkyl" as used herein, refers to an alkoxy group, as defined herein, appended to the parent molecular moiety through a fluoroalkyl group, as defined herein.

The term "aryl" as used herein, refers to a phenyl group, or a bicyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Representative examples of aryl include, but are not limited to, indolyl, naphthyl, phenyl, quinolinyl and tetrahydroquinolinyl.

The term "arylalkyl" as used herein, refers to an aryl group, as defined herein, appended to the parent molecular moiety through an alkyl group, as defined herein.

The term "arylsulfonyl" as used herein, refers to an aryl group, as defined herein, appended to the parent molecular moiety through a sulfonyl.

The term "carboxy" as used herein, refers to a carboxylic acid group, or COOH, where the carboxylic acid is appended to the parent molecular moiety through the carbon of the carboxylic acid.

The term "cycloalkyl" as used herein, refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl and cyclodecyl.

The term "cycloalkenyl" as used herein, refers to a carbocyclic ring system containing three to ten carbon atoms, zero heteroatoms and at least one double bond.

The term "fluoroalkyl" as used herein, refers to at least one fluorine atom appended to the parent molecular moiety through an alkyl group, as defined herein.

The term "fluoroalkoxy" as used herein, refers to at least one fluorine atom appended to the parent molecular moiety through an alkoxy group, as defined herein.

The term "halogen" or "halo" as used herein, means Cl, Br, I, or F.

The term "haloalkyl" as used herein, refers to at least one halogen atom appended to the parent molecular moiety through an alkyl group, as defined herein.

The term "haloalkoxy" as used herein, refers to at least one halogen atom appended to the parent molecular moiety through an alkoxy group, as defined herein.

The term "haloalkylcarbonyl" as used herein, refers to at least one haloalkyl, as defined herein, appended to the parent molecular moiety through a carbonyl group.

The term "haloalkoxycarbonyl" as used herein, refers to at least one haloalkoxy group, as defined herein, appended to the parent molecular moiety through a carbonyl group.

The term "haloalkylsulfonyl" as used herein, refers to a haloalkyl group, as defined herein, appended to the parent molecular moiety through a sulfonyl.

The term "heteroalkyl" as used herein, means an alkyl group, as defined herein, in which one or more of the carbon atoms has been replaced by a heteroatom selected from S, O, P and N. Representative examples of heteroalkyls include, but are not limited to, alkyl ethers, secondary and tertiary alkyl amines, amides, and alkyl sulfides.

The term "heteroaryl" as used herein, refers to an aromatic monocyclic ring or an aromatic bicyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl, thiazolyl, and quinolinyl.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S.

The term "heteroarylalkyl" as used herein, refers to a heteroaryl group, as defined herein, appended to the parent molecular moiety through an alkyl group, as defined herein.

The term "hydroxycarbonyl" as used herein, refers to a —C(O)—OH substituent.

The term "(hydroxycarbonyl)heteroalkyl" as used herein, refers to hydroxycarbonyl group appended to the parent molecular moiety through a heteroalkyl group, as defined herein. An exemplary (hydroxycarbonyl)heteroalkyl group is —SCH$_2$CO$_2$H.

The term "substituted" refers to a group that may be further substituted with one or more non-hydrogen substituent groups. Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

In some instances, the number of carbon atoms in a hydrocarbyl substituent (e.g., alkyl or cycloalkyl) is indicated by the prefix "C$_x$-C$_y$-", wherein x is the minimum and y is the maximum number of carbon atoms in the substituent. Thus, for example, "C$_1$-C$_3$-alkyl" refers to an alkyl substituent containing from 1 to 3 carbon atoms.

Certain substituent groups may be abbreviated herein. For example, the abbreviations Me and Et represent methyl and ethyl, respectively. A more comprehensive list of standard abbreviations used by organic chemists appears in a table entitled Standard List of Abbreviations of the Journal of Organic Chemistry. The abbreviations contained in said list are hereby incorporated by reference.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of" and "consisting essentially of," the embodiments or elements presented herein, whether explicitly set forth or not.

2. Methods of Synthesis

Classical syntheses of substituted rhodamine dyes, such as 6-carboxytetramethylrhodamine (TMR) suffer from a number of drawbacks. For example, such syntheses may require harsh reaction conditions and, as a result, may provide low yields of the desired products. The syntheses also produce mixtures of isomers, requiring extensive purification protocols to separate the products and provide the pure isomers. In the case of certain highly substituted rhodamine dyes, the aniline may be expensive to purchase or may require a complicated multi-step synthesis, and the consumption of half of the aniline in production of the undesired isomer can be particularly wasteful.

Scheme 1 illustrates the classical synthesis of 6-carboxytetramethylrhodamine (6-carboxy-TMR), which also produces 5-carboxytetramethylrhodamine (5-carboxy-TMR) as a byproduct. In this transformation, a carboxyl-substituted phthalic anhydride (1,3-dioxo-1,3-dihydroisobenzofuran-5-carboxylic acid) is reacted with an aminophenol (3-(dimethylamino)phenol) to form the mixture of 6-carboxy-TMR and 5-carboxy-TMR.

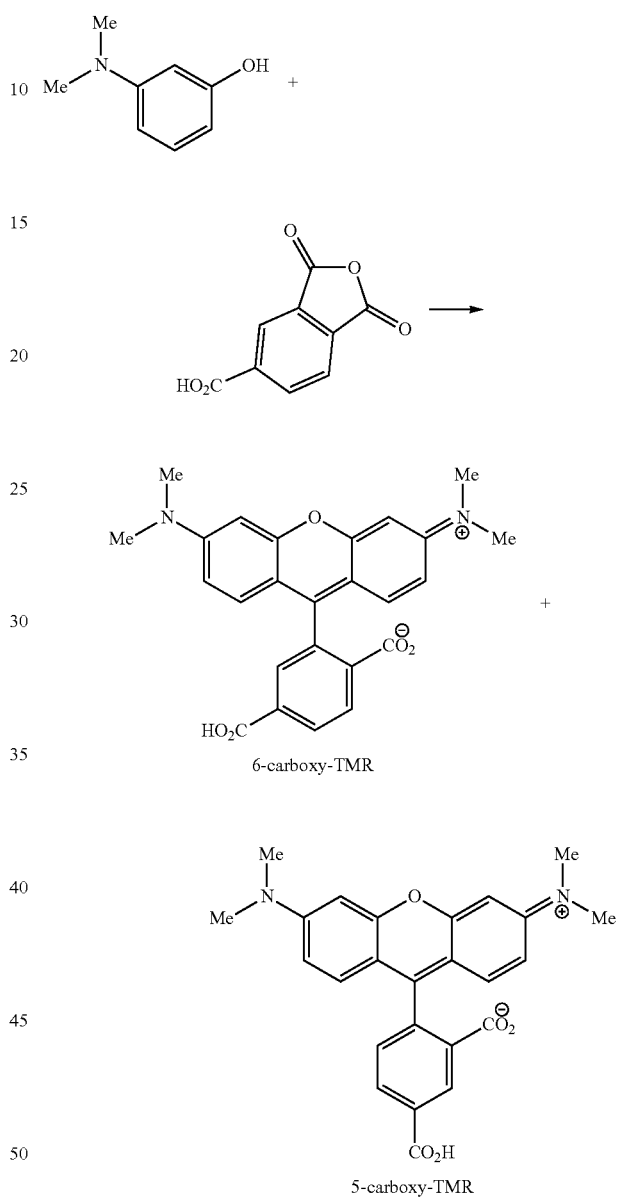

Scheme 1. Classical synthesis of 5(6)-carboxy-TMRs

The synthesis of other substituted rhodamine dyes that use substituted phthalic anhydrides as a starting material also suffer from a similar lack of regioselectivity.

These problems are addressed herein with the disclosure of a facile regioselective synthesis of rhodamine dyes (e.g. 5- and 6-position substituted rhodamine dyes), using substituted phthalaldehydic acids or phthalaldehydic acid derivatives as a starting material instead of substituted phthalic anhydrides. The reaction of a compound of formula (I) with a compound of formula (II) provides rhodamine dyes [compound of formula (III)] in high yields under mild conditions, and in isomerically pure form. Schematic representation of this process is illustrated in Scheme 2.

Scheme 2. New syntheses of rhodamine dyes

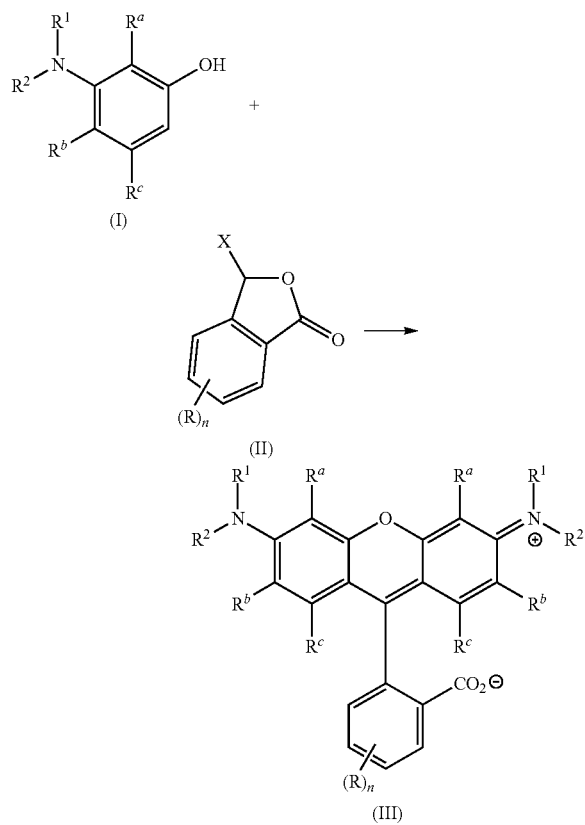

A. Compounds of Formula (I)

The method of synthesizing the rhodamine of the present disclosure may include a compound of formula (I):

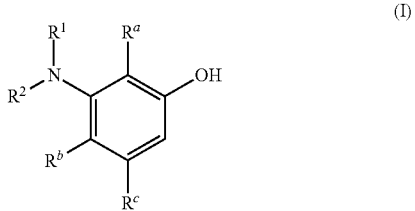

wherein:
R$^1$ and R$^2$ are each independently hydrogen, alkyl, or R$^{1a}$—CO—, wherein R$^{1a}$ is hydrogen, C$_1$-C$_4$ alkyl (e.g., tBu), C$_1$-C$_4$ haloalkyl (e.g., CF$_3$, CHF$_2$), or C$_1$-C$_4$ alkoxy; or R$^1$ and R$^2$, together with the atoms to which they are attached, form a 3-8 membered ring;

R$^c$ is selected from the group consisting of hydrogen, alkyl, alkoxy, haloalkyl and halogen; and R$^a$ and R$^b$ are each independently selected from the group consisting of hydrogen, alkyl, alkoxy, haloalkyl and halogen; or R$^1$ and R$^a$, together with the atoms to which they are attached, form a 5-8 membered ring, and R$^2$ and R$^b$, together with the atoms to which they are attached, form a 5-8 membered ring.

In some embodiments, the method of synthesizing the rhodamine of the present disclosure may include a compound of formula (I):

wherein:
R$^1$ and R$^2$ are each independently hydrogen and alkyl, or R$^1$ and R$^2$, together with the atoms to which they are attached, form a 3-8 membered ring, R$^c$ is selected from the group consisting of hydrogen, alkyl, alkoxy, haloalkyl and halogen; and R$^a$ and R$^b$ are each independently selected from the group consisting of hydrogen, alkyl, alkoxy, haloalkyl and halogen; or R$^1$ and R$^a$, together with the atoms to which they are attached, form a 5-8 membered ring, and R$^2$ and R$^b$, together with the atoms to which they are attached, form a 5-8 membered ring.

In some embodiments, R$^1$ and R$^2$ are each independently alkyl. In some embodiments, R$^1$ and R$^2$ are each independently C$_1$-C$_4$ alkyl. In some embodiments, R$^1$ and R$^2$ are each independently hydrogen. In some embodiments, one of R$^1$ or R$^2$ is C$_1$-C$_4$ alkyl and the other is hydrogen.

In some embodiments, R$^1$ and R$^a$, together with the atoms to which they are attached, form a 6- or 7-membered ring, and R$^2$ and R$^b$, together with the atoms to which they are attached, form a 6- or 7-membered ring. For example, in some embodiments, R$^1$ and R$^a$, together with the atoms to which they are attached, form a 6-membered ring, and R$^2$ and R$^b$, together with the atoms to which they are attached, also form a 6-membered ring. In some embodiments, R$^1$ and R$^a$, together with the atoms to which they are attached, form a 6-membered ring, and R$^2$ and R$^b$, together with the atoms to which they are attached, form a 7-membered ring.

In some embodiments, R$^a$ and R$^b$ are hydrogen. In some embodiments, R$^c$ is hydrogen. In some embodiments, R$^a$, R$^b$ and R$^c$ are each hydrogen.

Exemplary compounds of formula (I) include the following:

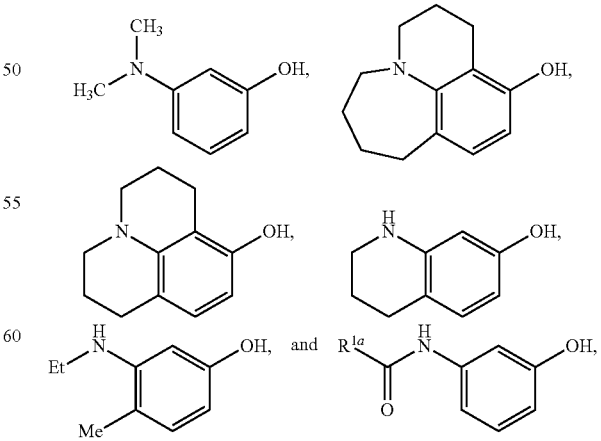

wherein R$^{1a}$ is hydrogen, C$_1$-C$_4$ alkyl (e.g., tBu), C$_1$-C$_4$ haloalkyl (e.g., CF$_3$, CHF$_2$), or C$_1$-C$_4$ alkoxy.

B. Compounds of Formula (II)

The method of synthesizing the rhodamine of the present disclosure may include a compound of formula (II):

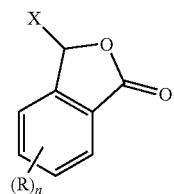

wherein:

R is selected from the group consisting of halogen, alkyl, haloalkyl, cyano, carboxy, alkoxy, haloalkoxy, alkoxycarbonyl, (hydroxycarbonyl)heteroalkyl, alkylcarbonyl, alkoxyalkyl, cycloalkyl, aryl, arylalkyl, heteroaryl, heteroarylalkyl, sulfonate, sulfonamide and amide;

n is 0, 1, 2, 3 or 4;

X is halogen or $OR^3$; and $R^3$ is selected from the group consisting of hydrogen, alkyl, aryl, alkylcarbonyl, alkoxycarbonyl, haloalkyl, haloalkylcarbonyl, haloalkoxycarbonyl, alkylsulfonyl, arylsulfonyl and haloalkylsulfonyl.

In some embodiments, X is halogen or $OR^3$; and $R^3$ is selected from the group consisting of hydrogen, alkyl, aryl and alkylcarbonyl.

In some embodiments, X is halogen or $OR^3$; and $R^3$ is hydrogen.

In some embodiments, X is bromine or $OR^3$; and $R^3$ is hydrogen.

In some embodiments, X is $OR^3$; and $R^3$ is hydrogen.

In some embodiments, R is selected from the group consisting of hydrogen, halogen, alkyl, haloalkyl, cyano, carboxy, alkoxycarbonyl and alkylcarbonyl.

In some embodiments, R is halogen or carboxy.

In some embodiments, the compound of formula (II) is selected from the group consisting of

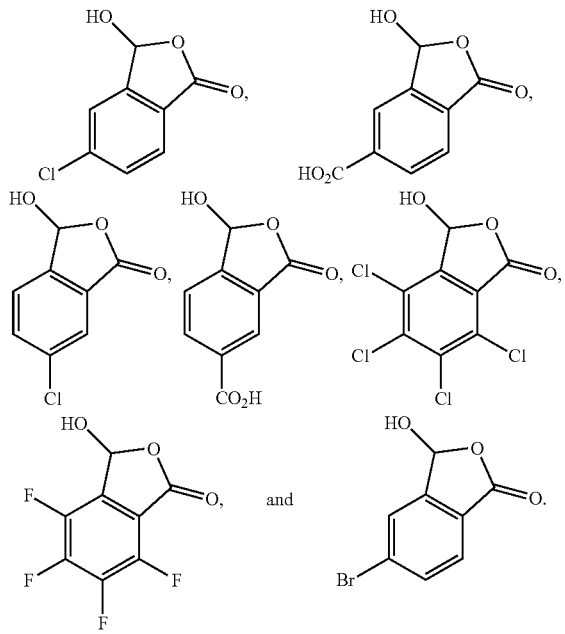

The compound of formula (II), when X is $OR^3$ and $R^3$ is H, may also be referred to as a "phthalaldehydic acid". The compound of formula (II), or the "phthalaldehydic acid" exists in an equilibrium between its closed and open forms:

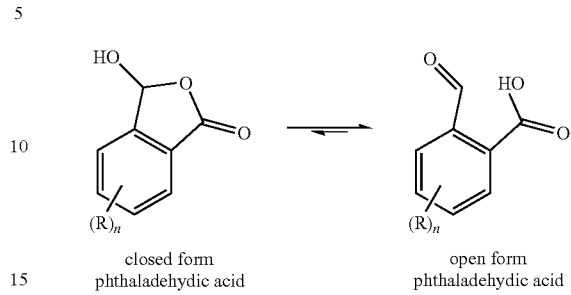

closed form
phthaladehydic acid open form
phthaladehydic acid

The compound of formula (II) may be substituted at the 4 position or the 5 position in certain embodiments. For example, "4-carboxyphthalaldehydic acid" and "5-carboxyphthalaldehydic acid" refer to the compounds having the following structural formula; these compound are also known as 3-hydroxy-1-oxo-1,3-dihydroisobenzofuran-5-carboxylic acid and 1-hydroxy-3-oxo-1,3-dihydroisobenzofuran-5-carboxylic acid:

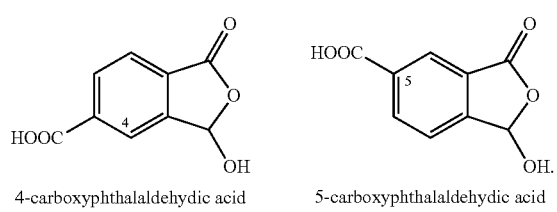 [SMILES: O=C(O)c1ccc2c(c1)C(O)OC2=O ; O=C(O)c1ccc2c(c1)C(=O)OC2O]

4-carboxyphthalaldehydic acid 5-carboxyphthalaldehydic acid

The synthesis of the compound of formula (II) may be accomplished through a variety of methods. For example, the 4- and 5-carboxyphthalaldehydic acids that are used in certain exemplary syntheses can be prepared from inexpensive starting materials via several protocols. They may be synthesized via a one-step palladium-catalyzed hydroxycarbonylation of appropriately substituted halo-benzaldehydes (Schemes 3a and 3b below).

Scheme 3. Syntheses of carboxyphthalaldehydic acids (a) General scheme for synthesis of phthalaldehydic acids via Pd-catalyzed hydroxycarbonylation

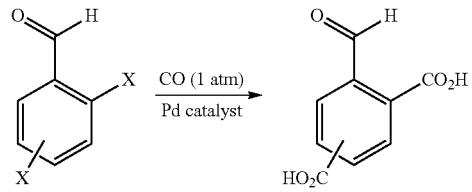

(b) Synthesis of 4-carboxyphthalaldehydic acid from 2,5-dibromobenzaldehyde

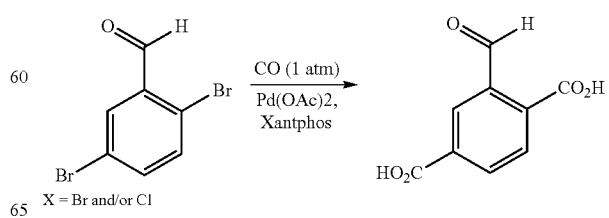

X = Br and/or Cl

In another embodiment, 4- and 5-halogen substituted phthalaldehydic acids used in certain exemplary syntheses can also be prepared in a similar manner. They may be synthesized via a selective one-step palladium-catalyzed hydroxycarbonylation of appropriately-substituted halobenzaldehydes shown in Scheme 4 below.

Scheme 4. Syntheses of halogen-substituted phthalaldehydic acids

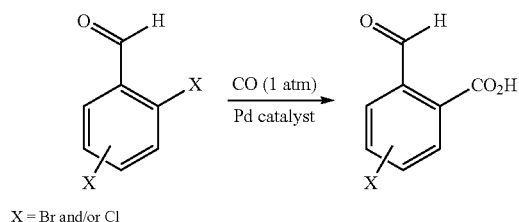

X = Br and/or Cl

Alternatively, carboxyphthalaldehydic acids may be synthesized from the corresponding benzolactone in a two-step sequence that proceeds through hydrolysis of a bromophthalide intermediate (Scheme 5).

Scheme 5. Synthesis of 4-carboxyphthalaldehydic acid from methyl 1-oxo-1,3-dihydroisobenzofuran-5-carboxylate

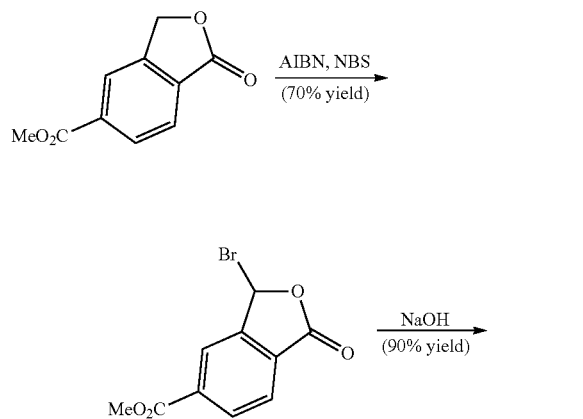

In similar fashion, other moieties which act as equivalents of a phthalaldehydic acid may be hydrolyzed to form desired substituted phthalaldehydic acids. As illustrated in Scheme 6, substituted phthalides (X=Br, OR$^3$; R$^3$=hydrogen, alkyl, aryl, alkylcarbonyl, alkoxycarbonyl, haloalkyl, haloalkylcarbonyl, haloalkoxycarbonyl, alkylsulfonyl, arylsulfonyl or haloalkylsulfonyl) may be hydrolyzed to provide substituted phthalaldehydic acids.

Scheme 6. Hydrolysis to form substituted phthalaldehydic acids

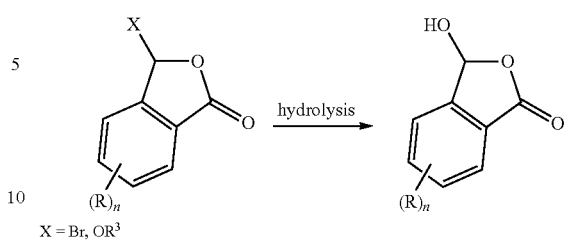

X = Br, OR$^3$

Other methods of synthesizing compounds of formula (II), such as substituted phthalaldehydic acids, will be evident to those of ordinary skill in the art. Additionally, certain synthetic steps described herein may be performed in an alternate sequence or order to give the desired compounds. Synthetic chemistry transformations and protecting group methodologies, i.e., protection and deprotection, useful in synthetic methods are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

C. Compounds of Formula (III)

The rhodamine dye may be a compound of formula (III),

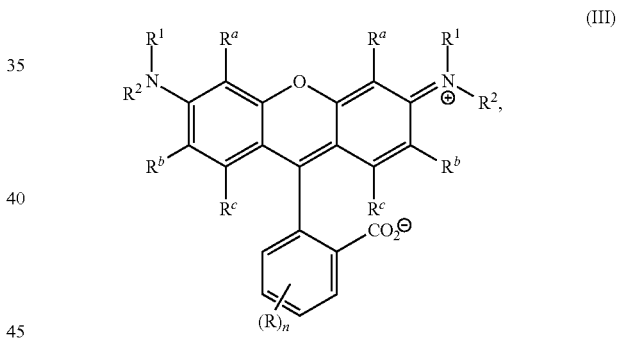

(III)

wherein:

R is selected from the group consisting of halogen, alkyl, haloalkyl, cyano, carboxy, alkoxy, haloalkoxy, alkoxycarbonyl, (hydroxycarbonyl)heteroalkyl, alkylcarbonyl, alkoxyalkyl, cycloalkyl, aryl, arylalkyl, heteroaryl, heteroarylalkyl, sulfonate, sulfonamide and amide;

n is 0, 1, 2, 3 or 4;

$R^1$ and $R^2$ are each independently hydrogen, alkyl, or $R^{1a}$—CO—, wherein $R^{1a}$ is hydrogen, $C_1$-$C_4$ alkyl (e.g., tBu), $C_1$-$C_4$ haloalkyl (e.g., $CF_3$, $CHF_2$), or $C_1$-$C_4$ alkoxy; or $R^1$ and $R^2$, together with the atoms to which they are attached, form a 3-8 membered ring;

$R^c$ is selected from the group consisting of hydrogen, alkyl, alkoxy, haloalkyl and halogen;

$R^a$ and $R^b$ are each independently selected from the group consisting of hydrogen, alkyl, alkoxy, haloalkyl and halogen; or $R^1$ and $R^a$, together with the atoms to which they are attached, form a 5-8 membered ring, and $R^2$ and $R^b$, together with the atoms to which they are attached, form a 5-8 membered ring.

In some embodiments, the rhodamine dye may be a compound of formula (III),

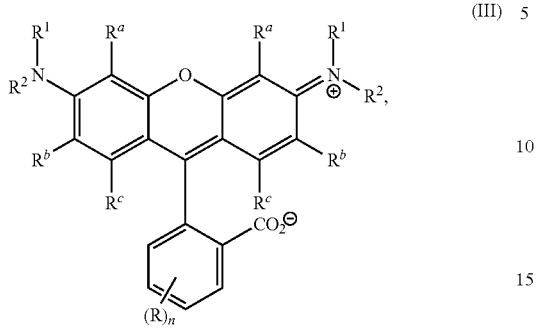

(III)

wherein:

R is selected from the group consisting of halogen, alkyl, haloalkyl, cyano, carboxy, alkoxy, haloalkoxy, alkoxycarbonyl, (hydroxycarbonyl)heteroalkyl, alkylcarbonyl, alkoxyalkyl, cycloalkyl, aryl, arylalkyl, heteroaryl, heteroarylalkyl, sulfonate, sulfonamide and amide;

n is 0, 1, 2, 3 or 4;

$R^1$ and $R^2$ are each independently hydrogen or alkyl, or $R^1$ and $R^2$, together with the atoms to which they are attached, form a 3-8 membered ring;

$R^c$ is selected from the group consisting of hydrogen, alkyl, alkoxy, haloalkyl and halogen;

$R^a$ and $R^b$ are each independently selected from the group consisting of hydrogen, alkyl, alkoxy, haloalkyl and halogen; or $R^1$ and $R^a$, together with the atoms to which they are attached, form a 5-8 membered ring, and $R^2$ and $R^b$, together with the atoms to which they are attached, form a 5-8 membered ring.

In some embodiments, R is selected from the group consisting of hydrogen, halogen, alkyl, haloalkyl, cyano, carboxy, alkoxycarbonyl and alkylcarbonyl.

In some embodiments, R is halogen or carboxy.

In some embodiments, n is 1. In some embodiments, n is 2. In some embodiments, n is 3. In some embodiments, n is 4.

In some embodiments, R is attached to the 5-position of the rhodamine.

In some embodiments, R is attached to the 6-position of the rhodamine.

In some embodiments, $R^1$ and $R^2$ are each independently alkyl.

In some embodiments, $R^1$ and $R^a$, together with the atoms to which they are attached, form a 6- or 7-membered ring, and $R^2$ and $R^b$, together with the atoms to which they are attached, form a 6- or 7-membered ring. For example, in some embodiments, $R^1$ and $R^a$, together with the atoms to which they are attached, form a 6-membered ring, and $R^2$ and $R^b$, together with the atoms to which they are attached, also form a 6-membered ring. In some embodiments, $R^1$ and $R^a$, together with the atoms to which they are attached, form a 6-membered ring, and $R^2$ and $R^b$, together with the atoms to which they are attached, form a 7-membered ring.

Exemplary compounds of formula (III) include the following:

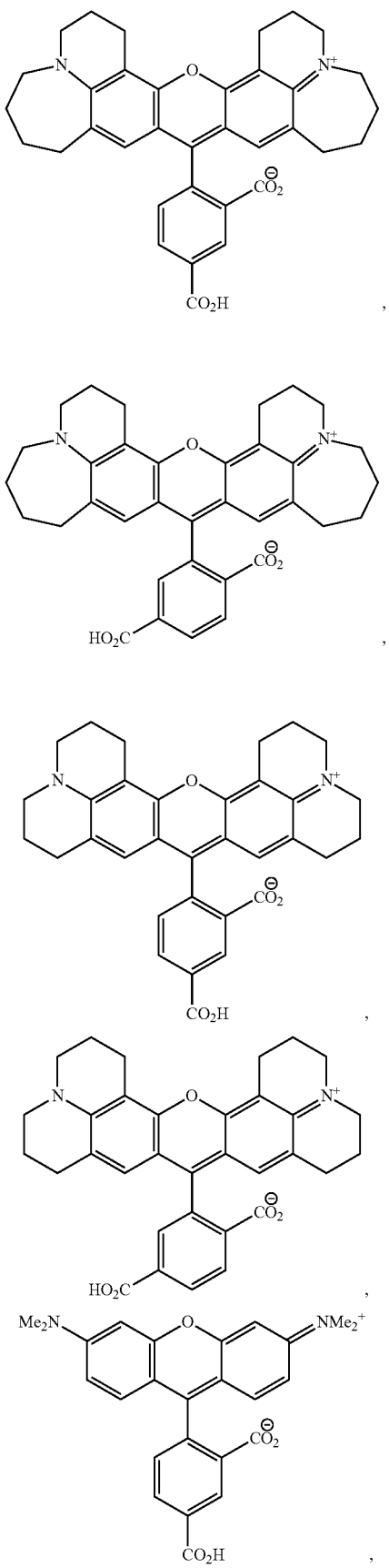

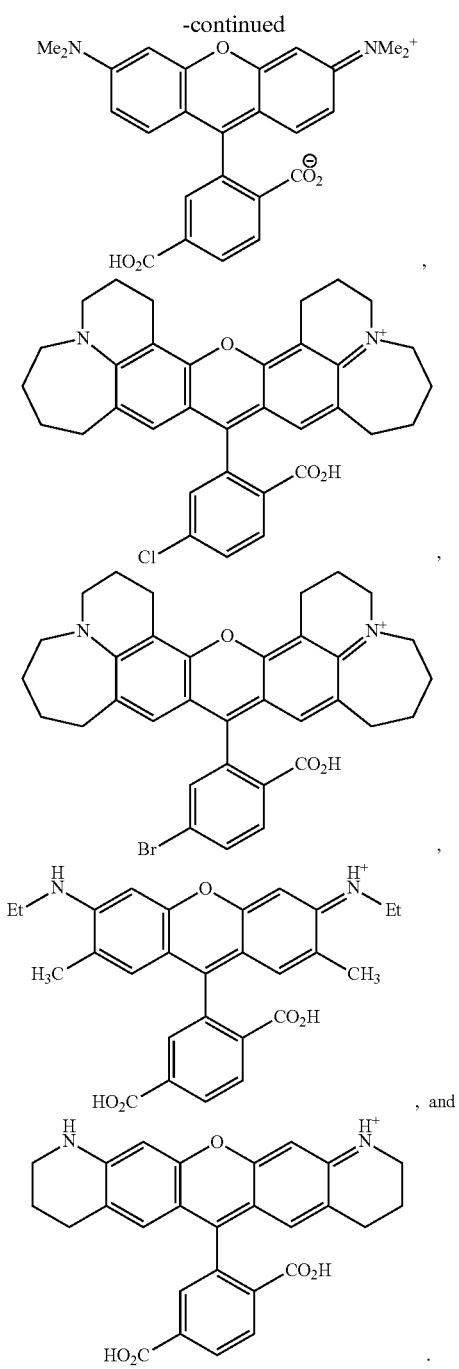

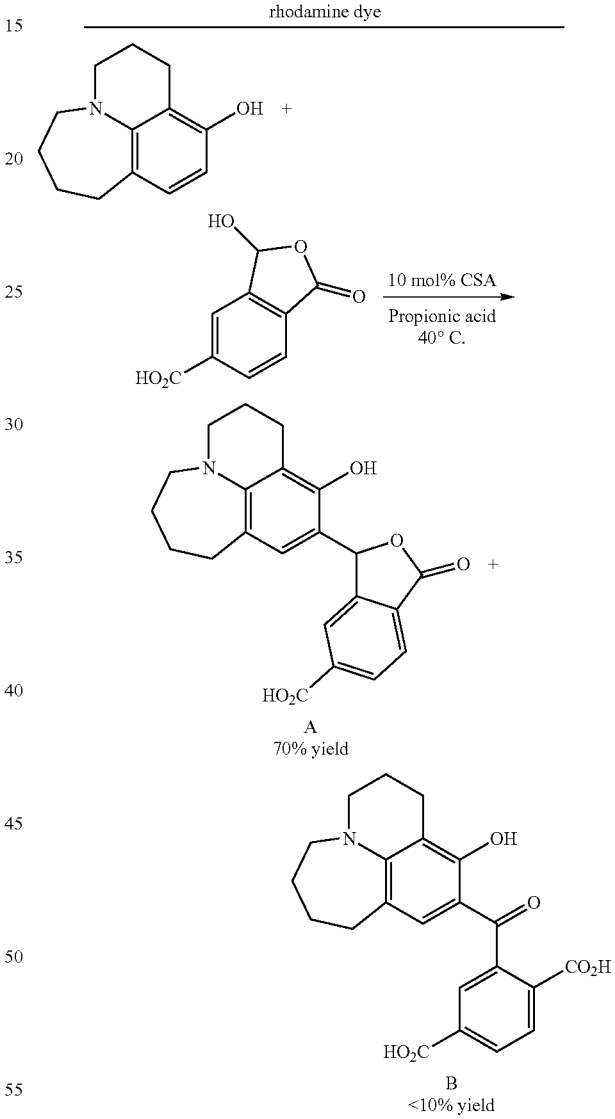

Scheme 7. Use of acidic conditions to attempt the synthesis of a rhodamine dye

A
70% yield

B
<10% yield

In general, two equivalents of the compound of formula (I) are required for double addition to the compound of formula (I) to form a symmetric rhodamine dye [compound of formula (III)] as shown above. In other embodiments, however, the rhodamine dye may be asymmetric. To achieve asymmetry, the rhodamine dye is synthesized by employing two different compounds of formula (I) in a reaction with the compound of formula (II).

D. Reaction Conditions

Reaction conditions typically used in the synthesis of rhodamines were employed in an attempt to synthesize rhodamine dyes of the present disclosure (Scheme 7). Specifically, 2,3,5,6,7,8-hexahydro-1H-azepino[3,2,1-ij]quinolin-11-ol was reacted with 4-carboxyphthalaldehydic acid in the presence of camphorsulfonic acid and propionic acid (solvent) at 40° C. to produce the single addition products A and B. Only trace amounts of the desired rhodamine dye were obtained. Under forcing reaction conditions (e.g., 80° C.), the lactone product reacted with a second equivalent of 2,3,5,6,7,8-hexahydro-1H-azepino[3,2,1-ij]quinolin-11-ol to give to give only a few percent of the dye. Similar results were obtained upon attempting the transformation without acid and replacing propionic acid with acetonitrile as the solvent.

It was determined that certain fluorinated alcohol solvents promote double addition of 2,3,5,6,7,8-hexahydro-1H-azepino[3,2,1-ij]quinolin-11-ol to substituted phthalaldehydic acids. Scheme 8 illustrates the double addition of 2,3,5,6,7,8-hexahydro-1H-azepino[3,2,1-ij]quinolin-11-ol to 4-chlorophthalaldehydic acid in 2,2,2-trifluoroethanol (TFE) under inert atmosphere to provide compound C, which was then converted to the rhodamine dye (6-Cl-NCT) after exposure to oxygen gas and heating.

Scheme 8. Double additional product and cyclization to the rhodamine dye

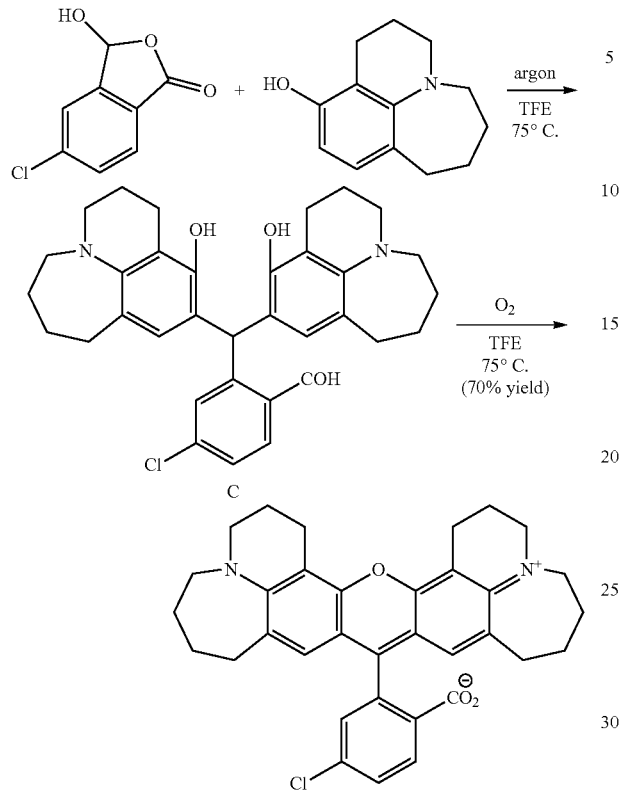

However, the same transformation was achieved in one step upon reaction of 2,3,5,6,7,8-hexahydro-1H-azepino[3,2,1-ij]quinolin-11-ol with 4-chlorophthalaldehydic acid under an atmosphere of oxygen ($O_2$ balloon) at 75° C. (Scheme 9).

Scheme 9. One step transformation to yield substituted rhodamine dye

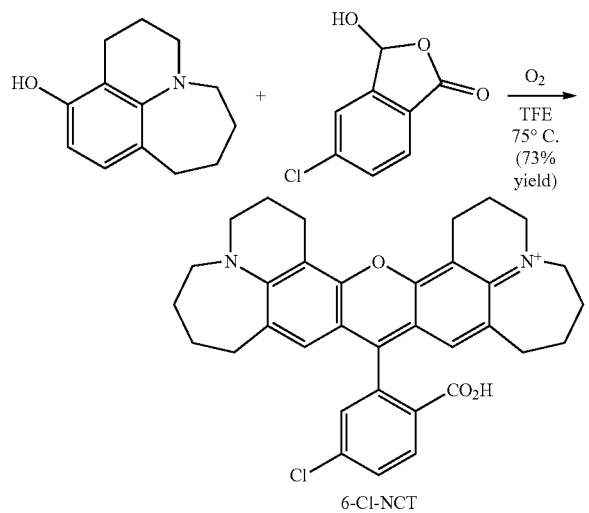

Exposure to the same reaction conditions resulted in the successful coupling of compound A with 2,3,5,6,7,8-hexahydro-1H-azepino[3,2,1-ij]quinolin-11-ol to provide the rhodamine dye, 6-Cl-NCT (Scheme 10).

Scheme 10. Formation of rhodamine dye from compound A

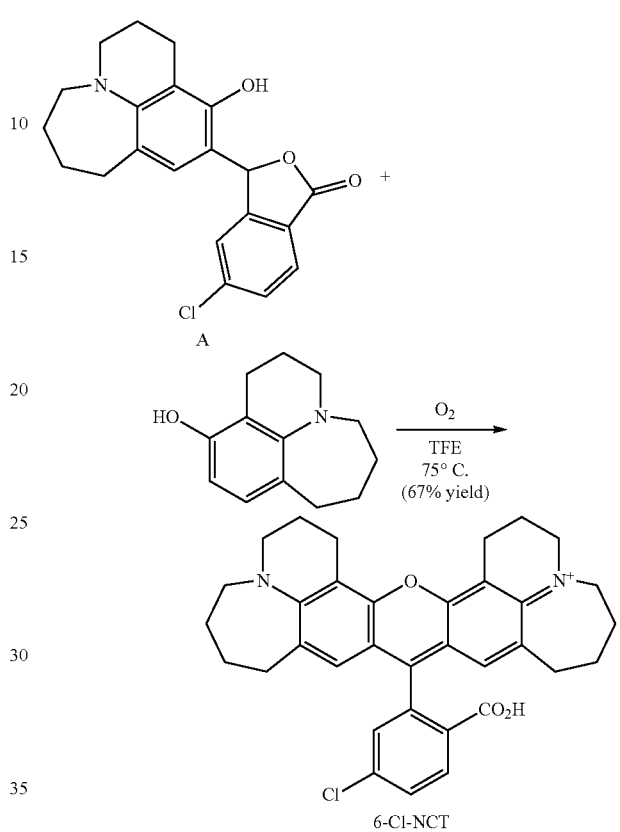

The reaction mixture comprising the compound of formula (I) and the compound of formula (II) may further comprise a solvent or mixture of solvents. Any suitable solvent that is compatible with the components of the reaction mixture may be used. Suitably, a solvent will be selected such that the starting materials will be at least partially soluble (or fully soluble) and will allow the reaction mixture to be heated, if necessary, to a temperature sufficient for the reaction to produce the desired rhodamine dye. The solvents may include, but are not limited to: ethers such as diethyl ether, dibutyl ether, 1,2-dimethoxyethane, diglyme, t-butyl methyl ether, tetrahydrofuran, dioxane, and the like; halogenated solvents such as chloroform, dichloromethane, dichloroethane, trifluorotoluene, chlorobenzene, 2,2,2-trifluoroethanol, hexafluoroisopropanol, and the like; aliphatic or aromatic hydrocarbon solvents such as benzene, xylene, toluene, hexane, pentane, and the like; esters and ketones such as ethyl acetate, acetone, 2-butanone, and the like; polar aprotic solvents such as acetonitrile, dimethylformamide, dimethylsulfoxide, and the like; polar protic solvents such as methanol, ethanol, n-propanol, isopropanol, n-butanol, acetic acid, water, and the like; or any combination of two or more solvents.

In certain embodiments, the solvent is a halogenated solvent. More specifically, the solvent is a fluorinated solvent, such as 2,2,2-trifluoroethanol or hexafluoroisopropanol. In other embodiments, the solvent may be a mixture of 2,2,2-trifluoroethanol and water. For example, the solvent may be a mixture of 2,2,2-trifluoroethanol and water, wherein the water comprises up to about 20% of the solvent mixture. The reaction may proceed more efficiently and in higher yield by the use of a fluorinated alcoholic solvent such as 2,2,2-trifluoroethanol.

In some embodiments, the method may further comprise heating the reaction mixture that comprises the compound of formula (I) and the compound of formula (II). For example, the reaction mixture may be heated to a temperature greater than ambient or room temperature, wherein ambient or room temperature is about 18° C. to about 25° C. The reaction mixture may be heated to a temperature of about 25° C. to about 100° C., or about 30° C. to about 80° C., e.g., to about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C.

Other components may also be added to the reaction mixture, such as an acid, a base or a salt.

The method of synthesizing the rhodamine may further comprise stirring the reaction mixture that comprises the compound of formula (I) and the compound of formula (II). For example, the reaction mixture may be stirred using a magnetic stirring bar, or an overhead mixer.

The reaction mixture comprising the compound of formula (I) and the compound of formula (II) may be contained within any suitable reaction vessel, such as a vial, flask, beaker, tube (e.g., a sealed tube), or the like. In some embodiments, the reaction vessel may be suitably dry, e.g., the reaction vessel may be dried in an oven and/or under vacuum.

In certain embodiments, the rhodamine dye can be synthesized under atmospheric conditions, i.e. at standard temperature and pressure, and not under an inert atmosphere. In other embodiments, the reaction may be conducted in the presence of an oxidizing agent. The oxidizing agent may be oxygen gas ($O_2$); ozone ($O_3$); hydrogen peroxide and other inorganic peroxides; fluorine, chlorine, and other halogens; nitric acid, potassium nitrate, and other nitrate compounds; sulfuric acid; peroxydisulfuric acid; peroxymonosulfuric acid; chlorite, chlorate and perchlorate compounds; hypochlorite compounds including bleach; hexavalent chromium compounds such as chromic acid, dichromic acid, chromium trioxide, and pyridinium chlorochromate; permanganate compounds such as potassium permanganate; sodium perborate; and nitrous oxide, or a combination thereof. In certain embodiments, the rhodamine dye can be synthesized under an atmosphere of oxygen gas. In other embodiments, oxygen gas may be bubbled through the reaction mixture. The reaction may proceed more efficiently and in higher yield by the use of oxygen gas as the oxidizing agent.

The method may comprise incubating, stirring and/or heating the reaction mixture for a period of time sufficient to form the rhodamine dye. For example, the reaction mixture may be incubated, stirred, and/or heated for about 30 minutes to about 24 hours, or about 1 hour to about 12 hours. For example, the reaction mixture may be incubated, stirred and/or heated for about 30 minutes, 1 hour, 1.5 hours, 2 hours, 2.5 hours, 3.0 hours, 3.5 hours, 4.0 hours, 4.5 hours, 5.0 hours, 5.5 hours, 6.0 hours, 6.5 hours, 7.0 hours, 7.5 hours, 8.0 hours, 8.5 hours, 9.0 hours, 9.5 hours, 10 hours, 10.5 hours, 11 hours, 11.5 hours, 12 hours, 13 hours, 14 hours, 15 hours, 16 hours, 17 hours, 18 hours, 19 hours, 20 hours, 21 hours, 22 hours, 23 hours or 24 hours.

The method may provide the rhodamine dye in a yield of about 50% to about 100%, e.g., about 60% to about 99%. For example, the method may provide the rhodamine dye in about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% yield.

In certain embodiments, the compound of formula (III) may be formed in a regioselective manner. The reaction may proceed in a manner such that compound of formula (III) is a mixture of regioisomers, which can be measured as a molar or weight ratio. The compound of formula (III) may be formed with a ratio of regioisomers greater than 2:1, greater than 3:1, greater than 4:1, greater than 5:1, greater than 6:1, greater than 7:1, greater than 8:1, greater than 9:1, greater than 10:1, greater than 11:1, greater than 12:1, greater than 13:1, greater than 14:1, greater than 15:1, greater than 16:1, greater than 17:1, greater than 18:1, greater than 19:1, greater than 20:1, greater than 25:1, greater than 30:1, greater than 40:1, greater than 50:1, greater than 60:1, greater than 70:1, greater than 80:1, greater than 90:1, or greater than 99:1.

The compound of formula (III) may be formed in a regioselective manner such that only one regioisomer is observed. The compound of formula (III) may be formed in a regioselective manner such that only one regioisomer is obtained upon isolation of the reaction product. For example, a 6-substituted rhodamine dye may be formed with substantially no formation of the corresponding 5-substituted rhodamine dye. Likewise, a 5-substituted rhodamine dye may be formed with substantially no formation of the corresponding 6-substituted rhodamine dye.

E. Optional Additional Method Steps

Methods of synthesizing the rhodamine dye may optionally further include additional process steps. For example, the method may further comprise the step of purifying the rhodamine dye from the reaction mixture. For example, the reaction mixture may be directly subjected to column chromatography (e.g., flash column chromatography) on a solid phase such as silica gel. The reaction mixture may alternatively be purified using other forms of chromatography, such as high pressure liquid chromatography (HPLC). The reaction mixture may be concentrated or the solvent may be removed prior to purification.

3. Examples

The foregoing may be better understood by reference to the following examples, which are presented for purposes of illustration and are not intended to limit the scope of the invention. All reagents and starting materials were purchased from commercial sources and used as received, or were synthesized from commercially-available starting materials according to known methods, unless indicated otherwise.

Synthesis of Phthaladehydic Acids

Synthesis 4-carboxyphthalaldehydic acid

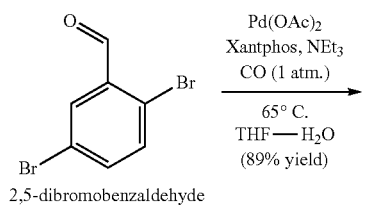

2,5-dibromobenzaldehyde

21
-continued

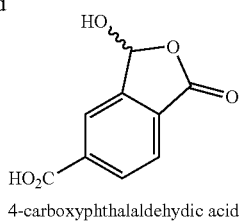

4-carboxyphthalaldehydic acid

A 500 mL round bottom flask, equipped with stir bar and septum, was charged with 2,5-dibromobenzaldehyde (3.10 g, 11.8 mmol), Pd(OAc)$_2$ (132 mg, 587 µmol) and Xantphos (680 mg, 1.17 mmol). The flask was evacuated and backfilled with argon (3× times repeat). Degassed THF (100 mL) was added, and the flask was evacuated and backfilled with carbon monoxide (3× times repeat). CO was allowed to bubble through the solution for 5 minutes while H$_2$O (7.5 mL) and Et$_3$N (6 mL) was added. The resulting dark brown solution (which turned light yellow over time) was heated to 65° C. under CO balloon for 20 hours at which point HPLC analysis indicated complete consumption of the starting material. The solvent was removed in vacuo, and the residue was partitioned between DCM (150 mL) and water (150 mL). Aqueous layer pH was adjusted to 10-11 with aq. 2M NaOH. Layers were separated and aqueous layer was washed 2×150 mL DCM. Aqueous layer was acidified to pH 2 with aq. 6M HCl (6M) and extracted with EtOAc (3×150 mL). Organic layers were combined, dried over Na$_2$SO$_4$, filtered and concentrated to provide 2.03 g (89% yield) of 4-carboxyphthalaldehydic acid as white solid. $^1$H NMR (300 MHz, DMSO-d$_6$) δ 13.61 (s, 1H), 8.47-8.22 (m, 1H), 8.18 (d, J=7.9 Hz, 1H), 8.13 (s, 1H), 7.94 (d, J=7.9 Hz, 1H); $^{13}$C NMR (75 MHz, DMSO-d$_6$) δ 167.7, 166.2, 147.7, 136.3, 131.5, 130.1, 124.9, 124.4, 98.4; HRMS (ESI+) calc'd for C$_9$H$_7$O$_5^+$ [M+H]$^+$ 195.0293. found 195.0285.

Synthesis 5-carboxyphthalaldehydic acid

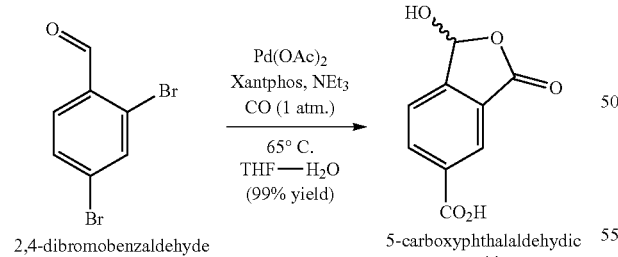

Using the same procedure as was used for the synthesis of 4-carboxyphthaladehydic acid described above, 5-carboxyphthalaldehydic acid was obtained in 99% yield as white solid. $^1$H NMR (300 MHz, DMSO-d$_6$) δ 13.61 (s, 1H), 8.47-8.22 (m, 1H), 8.18 (d, J=7.9 Hz, 1H), 8.13 (s, 1H), 7.94 (d, J=7.9 Hz, 1H); $^{13}$C NMR (75 MHz, DMSO-d$_6$) δ 167.7, 166.2, 147.7, 136.3, 131.5, 130.1, 124.9, 124.4, 98.4; HRMS (ESI+) calc'd for C$_9$H$_7$O$_5^+$ [M+H]$^+$ 195.0293. found 195.0285.

22
Synthesis 4-chlorophthalaldehydic acid

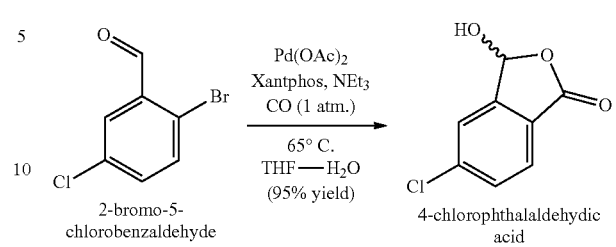

Using the same procedure as was used for the synthesis of 4-carboxyphthaladehydic acid described above, 4-chlorophthalaldehydic acid was obtained in 95% yield as white solid. $^1$H NMR (300 MHz, DMSO-d$_6$) δ 8.28 (s, 1H), 7.85 (d, J=8.1 Hz, 1H), 7.79 (d, J=1.8 Hz, 1H), 7.72 (d, J=8.1 Hz, 1H), 6.65 (s, 1H); $^{13}$C NMR (75 MHz, DMSO-d$_6$) δ 167.5, 149.4, 139.5, 131.0, 126.4, 125.5, 124.1, 97.7; HRMS (ESI+) calc'd for C$_8$H$_6$ClO$_3^+$ [M+H]$^+$ 185.0005. found 184.9994.

Example 1. Synthesis of 5-Carboxy-NCT

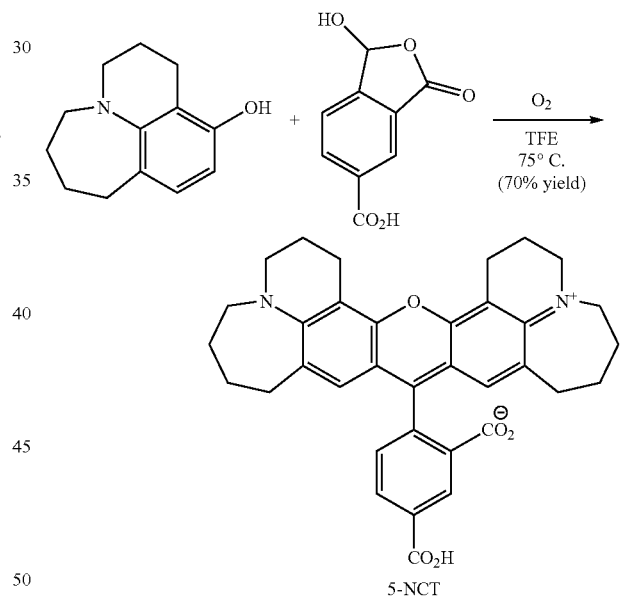

A 50 mL round-bottom flask equipped with a stir bar was charged with 5-carboxyphthalaldehydic acid (116 mg, 0.60 mmol), 2,3,5,6,7,8-hexahydro-1H-azepino[3,2,1-ij]quinolin-11-ol (255 mg, 1.25 mmol), and trifluoroethanol (25 mL). The preparation of 2,3,5,6,7,8-hexahydro-1H-azepino [3,2,1-ij]quinolin-11-ol is described in U.S. Pat. No. 9,056, 885, which is incorporated herein by reference in its entirety. Oxygen was allowed to bubble through the solution for 5 minutes. The resulting yellow solution was gently warmed under oxygen atmosphere to 75° C. and stirred vigorously for 20 hours. The solvent was concentrated in vacuo, and dark blue residue was purified by silica gel chromatography (0→60% MeOH/DCM) to provide 236 mg (70% yield) of 5-NCT as a dark blue solid. $^1$H NMR (300 MHz, DMSO-d$_6$) δ 13.48 (s, 1H), 8.39 (s, 1H), 8.27 (dd, J=8.1, 1.4 Hz, 1H), 7.37 (d, J=8.0 Hz, 1H), 6.26 (s, 2H), 3.19-3.12 (m, 4H), 3.05-3.00 (m, 4H), 2.93-2.87 (m, 4H), 2.52 (m, 4H, overlap with DMSO-$d_5$), 1.86-1.80 (m, 4H), 1.71-1.65 (m, 4H), 1.49-1.41 (m, 4H); $^{13}$C NMR (75 MHz, DMSO-$d_6$) δ 167.9, 166.1, 155.6, 150.2, 147.3, 135.8, 133.1, 129.9, 127.0, 125.4, 125.0, 124.6, 114.2, 108.5, 56.0, 53.1, 33.5, 29.1, 25.2, 21.7, 18.2; HRMS (ESI+) calc'd for $C_{35}H_{35}N_2O_5^+$ [M+H]$^+$ 563.2540. found 563.2541.

Example 2. Synthesis of 6-Carboxy-NCT

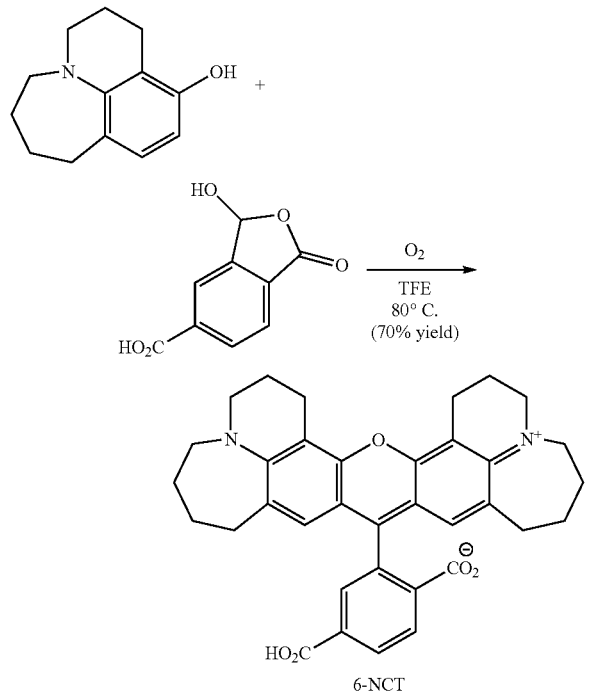

6-NCT

A 50 mL round-bottom flask equipped with a stir bar was charged with 4-carboxyphthalaldehydic acid (102 mg, 0.53 mmol), 2,3,5,6,7,8-hexahydro-1H-azepino[3,2,1-ij]quinolin-11-ol (320 mg, 1.57 mmol), and trifluoroethanol (25 mL). Oxygen was allowed to bubble through the solution for 5 minutes. The resulting yellow solution was gently warmed under oxygen atmosphere to 80° C. and stirred vigorously for 18 hours. The solvent was concentrated in vacuo, and dark blue residue was purified by silica gel chromatography (0→50% MeOH/DCM) to provide 206 mg (70% yield) of 6-NCT as a dark blue solid. $^1$H NMR (300 MHz, DMSO-$d_6$) δ 8.21 (dd, J=8.0, 1.3 Hz, 1H), 8.09 (dd, J=8.0, 0.6 Hz, 1H), 7.61 (dd, J=1.2, 0.7 Hz, 1H), 6.27 (s, 2H), 3.20-3.13 (s, 4H), 3.07-3.01 (m, 4H), 2.89 (t, J=6.5 Hz, 4H), 2.52 (m, 4H, overlap with DMSO-$d_5$), 1.87-1.77 (m, 4H), 1.71-1.62 (m, 4H), 1.49-1.40 (m, 4H); $^{13}$C NMR (75 MHz, DMSO-$d_6$) δ 166.0, 165.7, 155.62, 154.3, 151.1, 134.7, 134.1, 133.7, 131.4, 131.0, 130.8, 129.9, 128.3, 113.3, 108.6, 52.9, 52.4, 31.8, 25.2, 23.5, 20.2, 20.0; HRMS (ESI+) calc'd for $C_{35}H_{35}N_2O_5^+$ [M+H]$^+$ 563.2540. found 563.2540.

Example 3. Synthesis of 5-Carboxy-ROX

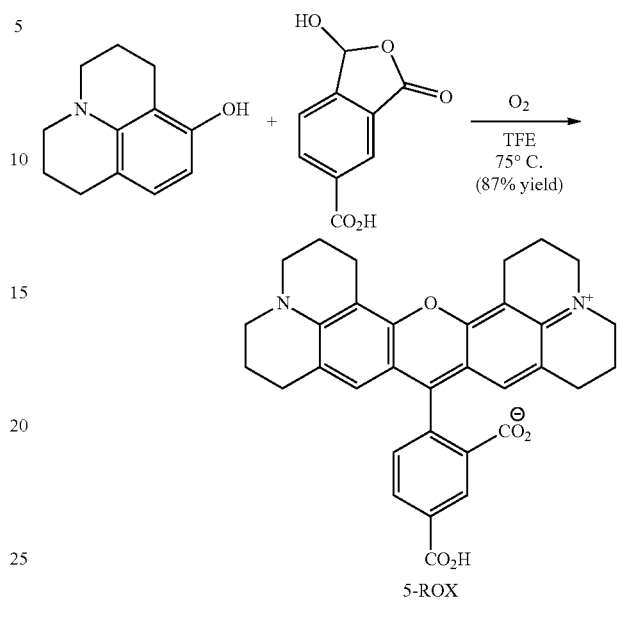

5-ROX

In a 50 mL round-bottom flask equipped with stir bar, 5-carboxyphthalaldehydic acid (116 mg, 0.60 mmol), 2,3,6,7-tetrahydro-1H,5H-pyrido[3,2,1-ij]quinolin-8-ol (238 mg, 1.25 mmol) and trifluoroethanol (25 mL). Oxygen was allowed to bubble through the solution for 5 minutes. The resulting dark brown solution was gently warmed up under oxygen atmosphere to 75° C. and stirred vigorously for 21 hours. The solvent was concentrated in vacuo, and dark blue residue was purified by silica gel chromatography (0→60% MeOH/DCM) to provide 279 mg (87% yield) of 5-ROX as a dark blue solid. $^1$H NMR (300 MHz, $CD_2Cl_2$-TFIP-$d_2$) δ 8.77 (d, J=1.6 Hz, 1H), 8.28 (dd, J=7.9, 1.8 Hz, 1H), 7.40 (d, J=8.0 Hz, 1H), 6.66 (s, 2H), 3.55-3.42 (m, 8H), 3.11 (t, J=6.3 Hz, 4H), 2.70 (t, J=6.0 Hz, 4H), 2.19-2.09 (m, 4H), 2.03-1.94 (m, 4H); $^{13}$C NMR (75 MHz, $CD_2Cl_2$-TFIP-$d_2$) δ 174.0, 171.2, 155.9, 153.4, 152.6, 139.4, 135.90, 134.1, 133.4, 132.9, 132.1, 126.8, 125.5, 113.7, 106.6, 51.9, 51.4, 28.2, 21.4, 20.8, 20.5; HRMS (ESI+) calc'd for $C_{33}H_{31}N_2O_5^+$ [M+H]$^+$ 535.2227. found 535.2228.

Example 4. Synthesis of 6-Carboxy-ROX

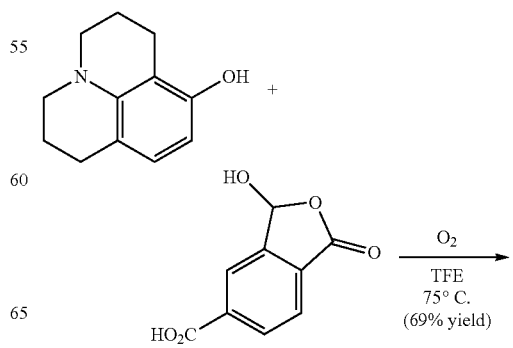

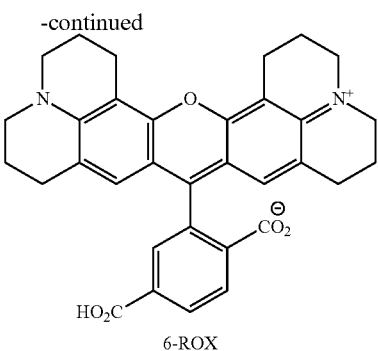

6-ROX

A 500 mL round-bottom flask equipped with stir bar was charged with 4-carboxyphthalaldehydic acid (1.0 g, 5.15 mmol), 2,3,6,7-tetrahydro-1H,5H-pyrido[3,2,1-ij]quinolin-8-ol (2.24 g, 11.9 mmol), and trifluoroethanol (6 mL). Two large oxygen balloons (ca 8 L of $O_2$) were attached through septa. The reaction was heated to 80° C. for 20 hours, at which point HPLC analysis indicated complete consumption of the starting material. Solvent was removed in vacuo and purified by silica gel chromatography (0→50% MeOH/DCM) to provide 2.27 g (82%) of 6-ROX as a dark blue-purple solid. $^1$H NMR (300 MHz, $CD_2Cl_2$-TFIP-$d_2$) δ 8.26 (s, 2H), 7.83 (s, 1H), 6.68 (s, 2H), 3.54-3.43 (m, 8H), 3.11 (t, J=6.4 Hz, 4H), 2.71 (t, J=6.1 Hz, 4H), 2.15 (p, J=6.3 Hz, 4H); $^{13}$C NMR (75 MHz, $CD_2Cl_2$-TFIP-$d_2$) δ 173.8, 171.9, 155.9, 153.5, 152.6, 137.4, 137.0, 135.6, 132.5, 132.2, 131.8, 126.9, 125.6, 114.0, 106.7, 51.9, 51.4, 28.3, 21.4, 20.8, 20.56; HRMS (ESI+) calc'd for $C_{33}H_{31}N_2O_5^+$ [M+H]$^+$ 535.2227. found 535.2228.

Example 5. Synthesis of 5-Carboxy-TMR

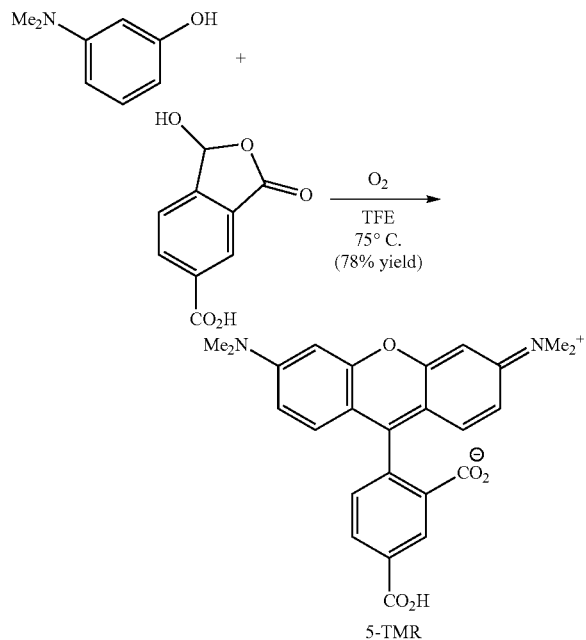

5-TMR

A 50 mL round-bottom flask equipped with stir bar was charged with 5-carboxyphthalaldehydic acid (84.0 mg, 0.43 mmol), 3-(dimethylamino)phenol (237 mg, 1.73 mmol), and trifluoroethanol (20 mL). Oxygen was allowed to bubble through the solution for 5 minutes. The resulting dark brown solution was gently warmed up under oxygen atmosphere to 75° C. and stirred vigorously for 22 hours. The solvent was concentrated in vacuo, and dark blue residue was purified by silica gel chromatography (0→60% MeOH/DCM) to provide 146 mg (78% yield) of 5-TMR as a dark blue solid. $^1$H NMR (300 MHz, DMSO-$d_6$) 8.38 (s, 1H), 8.27 (d, J=7.8 Hz, 1H), 7.14 (d, J=7.9 Hz, 1H), 6.53-6.45 (m, 6H), 2.93 (s, 12H); $^{13}$C NMR (75 MHz, DMSO-$d_6$) δ 169.0, 167.6, 153.6, 152.1, 151.9, 140.5, 136.0, 128.4, 126.3, 124.6, 123.1, 108.9, 106.1, 98.0, 84.3, 39.8 (overlap with DMSO-$d_6$); HRMS (ESI+) calc'd for $C_{25}H_{23}N_2O_5^+$ [M+H]$^+$ 431.1601. found 431.1601.

Example 6. Synthesis of 6-Carboxy-TMR

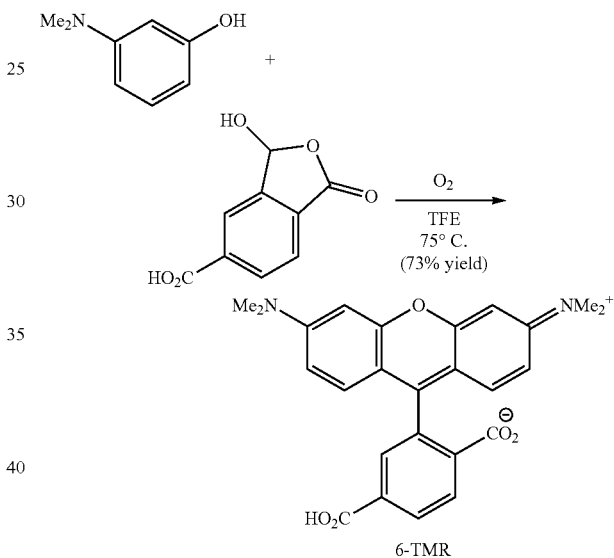

6-TMR

A 50 mL round-bottom flask equipped with stir bar was charged with 4-carboxyphthalaldehydic acid (89.0 mg, 0.46 mmol), 3-(dimethylamino)phenol (252 mg, 1.83 mmol), and trifluoroethanol (20 mL). Oxygen was allowed to bubble through the solution for 5 minutes. The resulting dark brown solution was gently warmed up under oxygen atmosphere to 75° C. and stirred vigorously for 22 hours. The solvent was concentrated in vacuo, and dark blue residue was purified by silica gel chromatography (0→60% MeOH/DCM) to provide 145 mg (73% yield) of 6-TMR as a dark blue solid. $^1$H NMR (300 MHz, Methanol-$d_4$) δ 8.40 (dd, J=8.2, 0.7 Hz, 1H), 8.36 (dd, J=8.2, 1.5 Hz, 1H), 7.95 (dd, J=1.6, 0.7 Hz, 1H), 7.12 (d, J=9.5 Hz, 2H), 7.03 (dd, J=9.5, 2.4 Hz, 2H), 6.95 (d, J=2.4 Hz, 2H), 3.28 (s, 12H, overlap with $CD_2HOD$); $^{13}$C NMR (75 MHz, Methanol-$d_4$) δ 166.3, 165.9, 159.0, 157.7, 157.5, 134.6, 134.5, 134.0, 131.4, 130.9, 130.9, 130.5, 114.2, 113.5, 96.1, 39.5; calc'd for $C_{25}H_{23}N_2O_5^+$ [M+H]$^+$ 431.1601. found 431.1607.

Example 7. Synthesis of 6-Chloro-NCT

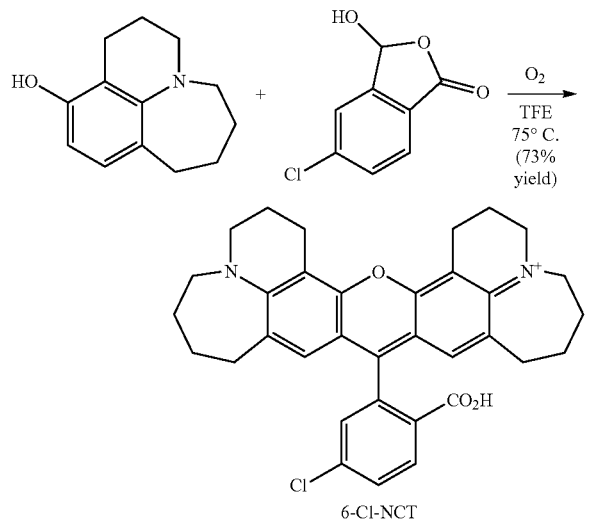

6-Cl-NCT

A 50 mL round-bottom flask equipped with stir bar was charged with 4-chlorophthalaldehydic acid (85.0 mg, 0.46 mmol), 2,3,5,6,7,8-hexahydro-1H-azepino[3,2,1-ij]quinolin-11-ol (197 mg, 0.97 mmol), and trifluoroethanol (20 mL). Oxygen was allowed to bubble through the solution for 5 minutes. The resulting clear yellow solution was gently warmed up under oxygen atmosphere to 75° C. A deep red color appeared after 10 minutes, and the resulting colored solution was stirred vigorously for 18 hours. The solvent was evaporated in vacuo, and dark blue residue was purified by silica gel chromatography (0→60% MeOH/DCM) to provide 200 mg (78% yield) of 6-Cl-NCT as a dark blue solid. $^1$H NMR (300 MHz, DMSO-$d_6$) δ 7.99 (dd, J=8.2, 0.6 Hz, 1H), 7.75 (dd, J=8.2, 1.8 Hz, 1H), 7.43 (dd, J=1.8, 0.6 Hz, 1H), 6.26 (s, 2H), 3.15 (m, 4H), 2.88 (m, 4H), 2.54 (m, 4H), 1.83 (m, 4H), 1.46 (m, 4H); $^{13}$C NMR (75 MHz, DMSO-$d_6$) δ 167.8, 154.2, 150.3, 147.3, 140.4, 130.6, 130.2, 126.5, 125.4, 125.0, 124.2, 114.4, 108.4, 84.3, 56.2, 53.2, 33.7, 29.3, 25.3, 21.8, 18.2; HRMS (ESI+) calc'd for $C_{34}H_{34}ClN_2O_3^+$ [M+H]$^+$ 553.2252. found 553.2251.

Example 8. Synthesis of 6-Bromo-NCT

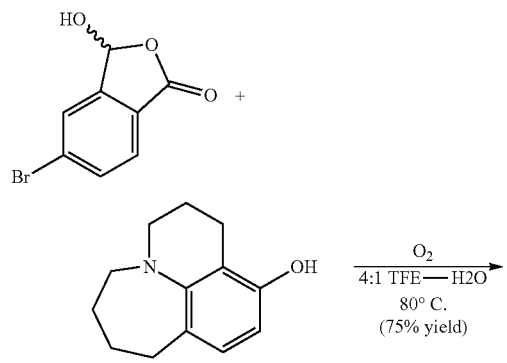

-continued

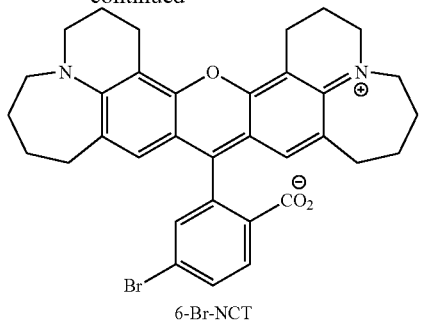

6-Br-NCT

A 50 mL round-bottom flask equipped with stir bar was charged with 4-bromophthalaldehydic acid (75.0 mg, 328 μmol), 2,3,5,6,7,8-hexahydro-1H-azepino[3,2,1-ij]quinolin-11-ol (140 mg, 688 μmol), water (4 mL), and trifluoroethanol (16 mL). Oxygen was allowed to bubble through the solution for 5 minutes. The resulting clear yellow solution was gently warmed up under oxygen atmosphere to 80° C. The resulting solution was stirred vigorously for 20 hours. Solvent was evaporated in vacuo, and dark blue residue was purified by silica gel chromatography (0→50% MeOH/DCM to provide 147 mg (75% yield) of 6-Br-NCT as a dark blue solid. $^1$H NMR (300 MHz, CD$_2$Cl$_2$) δ 7.85 (d, J=8.1 Hz, 1H), 7.73 (dd, J=8.2, 1.6 Hz, 1H), 6.31 (s, 2H), 3.28-3.13 (m, 4H), 3.12-3.02 (m, 4H), 3.01-3.84 (m, 4H), 2.66-2.52 (m, 4H), 1.99-1.81 (m, 4H), 1.80-1.69 (m, 4H), 1.62-1.43 (m, 4H); $^{13}$C NMR (75 MHz, CD$_2$Cl$_2$) δ 168.9, 154.9, 151.1, 148.5, 133.2, 130.9, 129.9, 127.9, 126.8, 126.6, 125.8, 115.1, 109.1, 57.2, 54.4 (overlap with CD$_2$Cl$_2$), 34.7, 30.0, 26.0, 22.6, 19.2; HRMS (ESI+) calc'd for $C_{34}H_{34}BrN_2O_3^+$ [M+H]$^+$ 597.1747. found 597.1735.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

The invention claimed is:

1. A method of synthesizing a rhodamine dye, the method comprising:
   reacting a compound of formula (I):

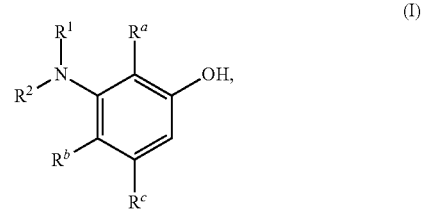

wherein
  $R^1$ and $R^2$ are each independently hydrogen, alkyl, or $R^{1a}$—CO—, wherein $R^{1a}$ is hydrogen, $C_1$-$C_4$ alkyl, $C_1$-$C_4$ haloalkyl, or $C_1$-$C_4$ alkoxy; or $R^1$ and $R^2$, together with the atoms to which they are attached, form a 3-8 membered ring;

R$^c$ is selected from the group consisting of hydrogen, alkyl, alkoxy, haloalkyl and halogen; and R$^a$ and R$^b$ are each independently selected from the group consisting of hydrogen, alkyl, alkoxy, haloalkyl and halogen; or R$^1$ and R$^a$, together with the atoms to which they are attached, form a 5-8 membered ring, and R$^2$ and R$^b$, together with the atoms to which they are attached, form a 5-8 membered ring;

with a compound of formula (II),

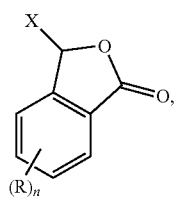

(II)

wherein

R is selected from the group consisting of halogen, alkyl, haloalkyl, cyano, carboxy, alkoxy, haloalkoxy, alkoxycarbonyl, (carboxyl)heteroalkyl, alkylcarbonyl, alkoxyalkyl, cycloalkyl, aryl, arylalkyl, heteroaryl, heteroarylalkyl, sulfonate, sulfonamide and amide;

n is 0, 1, 2, 3 or 4;

X is halogen or OR$^3$; and R$^3$ is selected from the group consisting of hydrogen, alkyl, aryl, alkylcarbonyl, alkoxycarbonyl, haloalkyl, haloalkylcarbonyl, haloalkoxycarbonyl, alkylsulfonyl, arylsulfonyl and haloalkylsulfonyl;

to form the rhodamine dye.

2. The method of claim 1, wherein R is selected from the group consisting of hydrogen, halogen, alkyl, haloalkyl, cyano, carboxy, alkoxycarbonyl and alkylcarbonyl.

3. The method of claim 1, wherein R is attached to the 4 or 5 position of the compound of formula (II).

4. The method of claim 1, wherein the compound of formula (II) is selected from the group consisting of

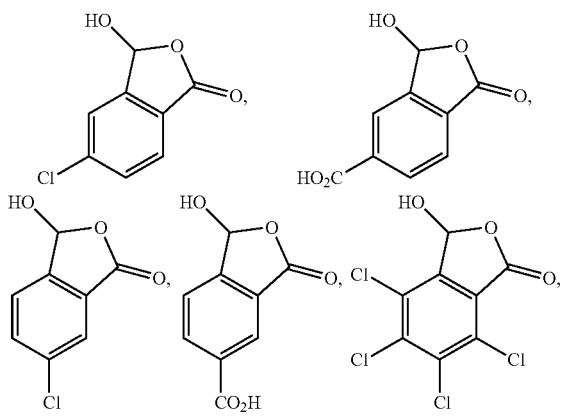

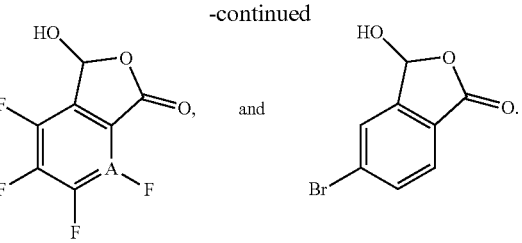

5. The method of claim 1, wherein X is OR$^3$; and R$^3$ is hydrogen.

6. The method of claim 1, wherein R$^1$ and R$^2$ are each independently C$_1$-C$_4$ alkyl.

7. The method of claim 1, wherein R$^c$ is hydrogen.

8. The method of claim 1, wherein R$^1$ and R$^a$, together with the atoms to which they are attached, form a 6- or 7-membered ring; and R$^2$ and R$^b$, together with the atoms to which they are attached, form a 6- or 7-membered ring.

9. The method of claim 1, wherein the compound of formula (I) is selected from the group consisting of:

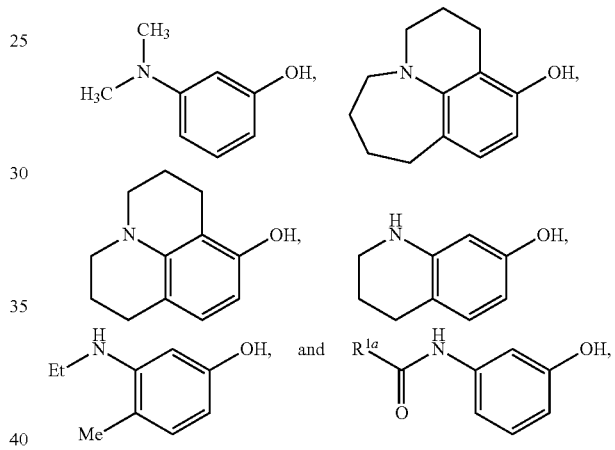

10. The method of claim 1, wherein the compound of formula (I) and the compound of formula (II) are reacted in at least one solvent.

11. The method of claim 10, wherein the solvent is a halogenated solvent, water, or a combination thereof.

12. The method of claim 1, wherein the compound of formula (I) and the compound of formula (II) are reacted in the presence of an oxidizing agent.

13. The method of claim 12, wherein the oxidizing agent is oxygen gas.

14. The method of claim 1, wherein oxygen is bubbled through the reaction of compound of formula (I) and the compound of formula (II).

15. The method of claim 1, wherein the compound of formula (I) and the compound of formula (II) are reacted at a temperature greater than ambient temperature.

16. The method of claim 1, wherein compound of formula (I) and the compound of formula (II) are heated to a temperature of about 30° C. to about 100° C.

17. The method of claim 1, further comprising purifying the rhodamine dye.

18. The method of claim 1, wherein the method produces a 6-substituted rhodamine dye with substantially no 5-substituted rhodamine byproduct or a 5-substituted rhodamine dye with substantially no 6-substituted rhodamine byproduct.

19. The method of claim 1, wherein the rhodamine dye is a compound of formula (III):

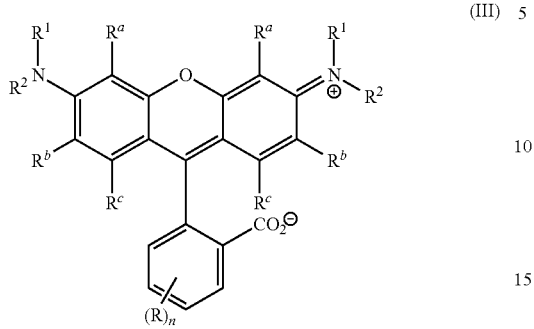

wherein:
R is selected from the group consisting of halogen, alkyl, haloalkyl, cyano, carboxy, alkoxy, haloalkoxy, alkoxycarbonyl, (carboxy)heteroalkyl, alkylcarbonyl, alkoxyalkyl, cycloalkyl, aryl, arylalkyl, heteroaryl, heteroarylalkyl, sulfonate, sulfonamide and amide;
n is 0, 1, 2, 3 or 4;
$R^1$ and $R^2$ are each independently hydrogen or alkyl or $R^{1a}$—CO—, wherein $R^{1a}$ is hydrogen, $C_1$-$C_4$ alkyl, $C_1$-$C_4$ haloalkyl, or $C_1$-$C_4$ alkoxy; or $R^1$ and $R^2$, together with the atoms to which they are attached, form a 3-8 membered ring;
$R^c$ is selected from the group consisting of hydrogen, alkyl, alkoxy, haloalkyl and halogen; and
$R^a$ and $R^b$ are each independently selected from the group consisting of hydrogen, alkyl, alkoxy, haloalkyl and halogen; or
$R^1$ and $R^a$, together with the atoms to which they are attached, form a 5-8 membered ring, and
$R^2$ and $R^b$, together with the atoms to which they are attached, form a 5-8 membered ring.

20. The method of claim 1, wherein the rhodamine dye is selected from the group consisting of:

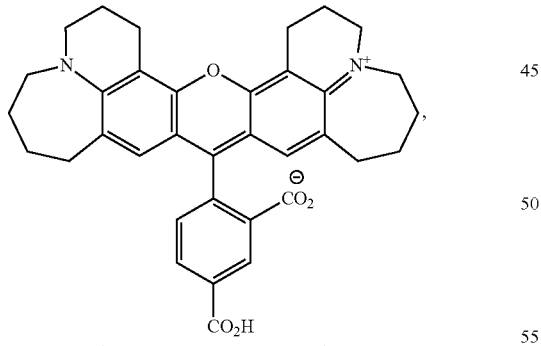

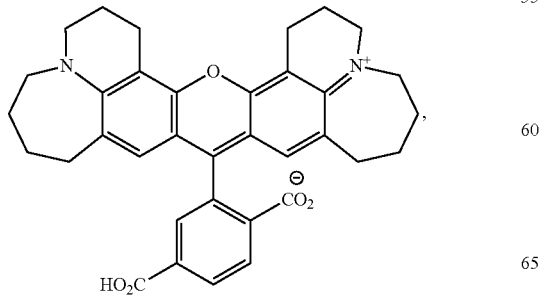

-continued

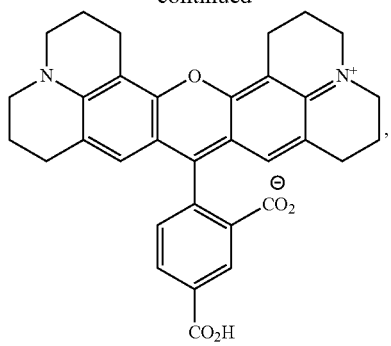

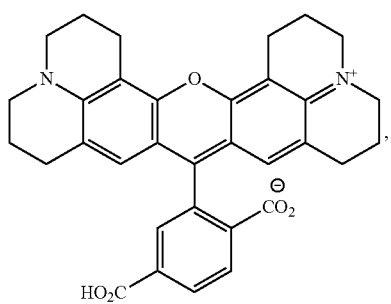

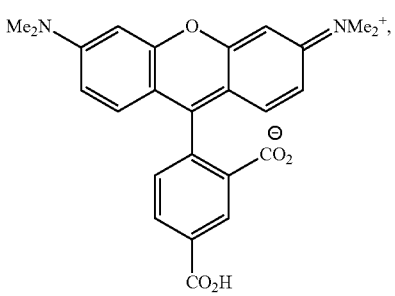

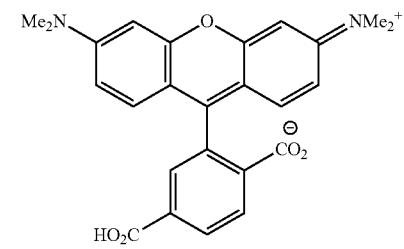

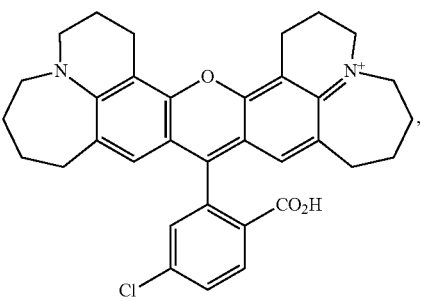

33
-continued
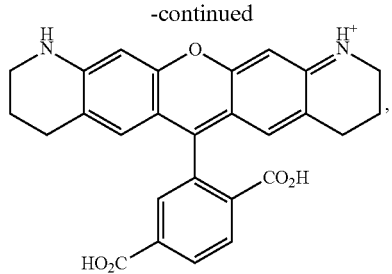
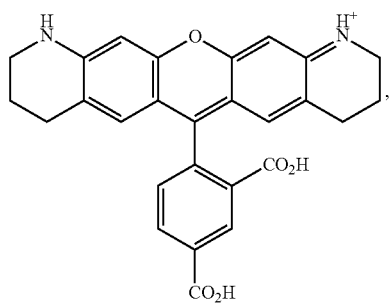
34
-continued
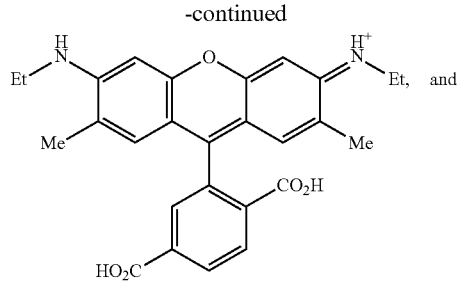, and
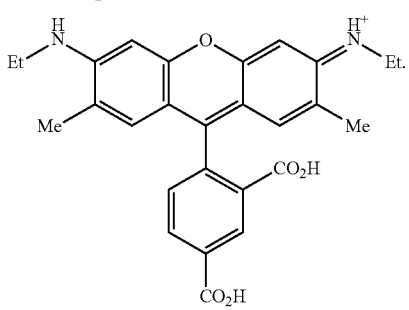
* * * * *

UNITED STATES PATENT AND TRADEMARK OFFICE
CERTIFICATE OF CORRECTION

| | | |
|---|---|---|
| PATENT NO. | : 10,093,806 B2 | Page 1 of 1 |
| APPLICATION NO. | : 15/282590 | |
| DATED | : October 9, 2018 | |
| INVENTOR(S) | : Stephen J. Dwight and Sergiy Levin | |

It is certified that error appears in the above-identified patent and that said Letters Patent is hereby corrected as shown below:

In the Claims

Claim 2, Column 29, Line 43 reads:
"group consisting of hydrogen, halogen, alkyl, haloalkyl,"

Whereas it should read:
"group consisting of halogen, alkyl, haloalkyl,"

Signed and Sealed this
Twenty-seventh Day of October, 2020

Andrei Iancu
*Director of the United States Patent and Trademark Office*